(12) United States Patent
Nahleili

(10) Patent No.: US 7,507,258 B2
(45) Date of Patent: Mar. 24, 2009

(54) POLYMERIC STENT USEFUL FOR THE TREATMENT OF THE SALIVARY GLAND DUCTS AND METHOD FOR USING THE SAME

(76) Inventor: Oded Nahleili, 41 Givati Street, Ashkelon (IL) 78471

( * ) Notice: Subject to any disclaimer, the term of this patent is extended or adjusted under 35 U.S.C. 154(b) by 0 days.

(21) Appl. No.: 11/682,031

(22) Filed: Mar. 5, 2007

(65) Prior Publication Data
US 2007/0162148 A1  Jul. 12, 2007

Related U.S. Application Data

(63) Continuation of application No. 10/507,304, filed as application No. PCT/IL02/00861 on Oct. 28, 2002, now Pat. No. 7,195,646.

(30) Foreign Application Priority Data
Mar. 11, 2002  (IL) .................................. 148616

(51) Int. Cl.
*A61F 2/04* (2006.01)
(52) U.S. Cl. ...................... 623/23.7; 623/23.64; 604/8
(58) Field of Classification Search .............. 623/23.64, 623/23.7, 1.31, 1.15, 1.36; 604/8
See application file for complete search history.

(56) References Cited

U.S. PATENT DOCUMENTS

| 3,788,327 A | 1/1974 | Donowitz et al. |
| 3,818,511 A | 6/1974 | Goldberg et al. |
| 4,973,301 A * | 11/1990 | Nissenkorn ............... 604/8 |
| 5,466,242 A | 11/1995 | Mori |
| 5,968,058 A * | 10/1999 | Richter et al. ............ 606/166 |

FOREIGN PATENT DOCUMENTS

| CH | 680263 | 7/1992 |
| GB | 1518654 | 7/1978 |

OTHER PUBLICATIONS

Nahlieli et al. "Diagnosis and treatment of strictures and kinks in salivary glad ducts"—J. Oral Maxillofac Surg—pp. 483-490.

* cited by examiner

*Primary Examiner*—Bruce E Snow
(74) *Attorney, Agent, or Firm*—Lowe Hauptman Ham & Berner, LLP

(57) ABSTRACT

A polymeric stent, especially useful in surgical endoscopy and for the treatment of salivary gland ducts comprising; an elongated tube (1), wherein the proximal end (3) of said tube is having a funnel-like shape; and wherein said funnel further comprise at least one gorge (5a), which enables the suturing of said stent to said duct. The invention also relates to a method for implanting the polymeric stent into the lumen of a salivary gland duct.

19 Claims, 4 Drawing Sheets

Figures 1A, 1B:
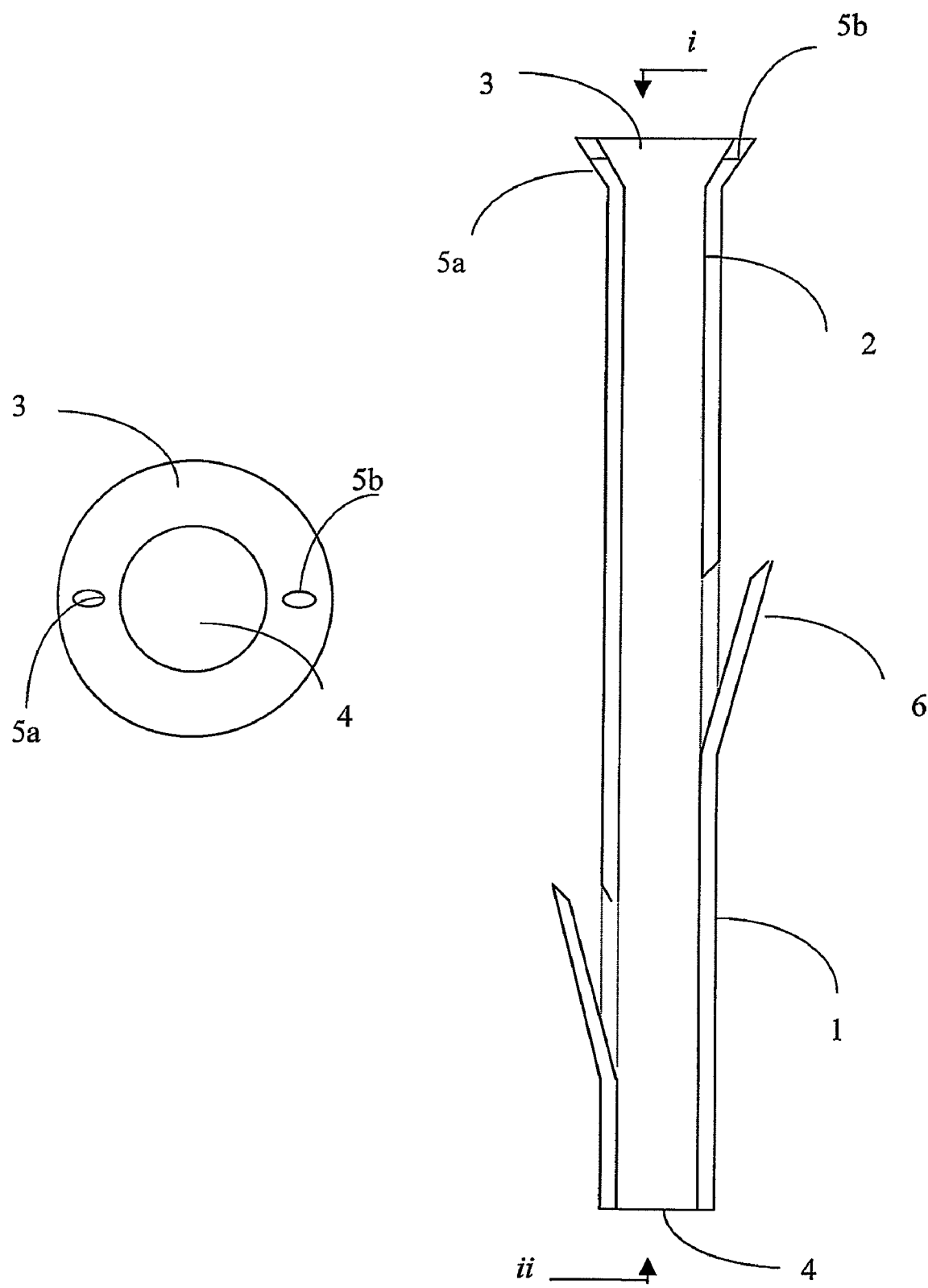

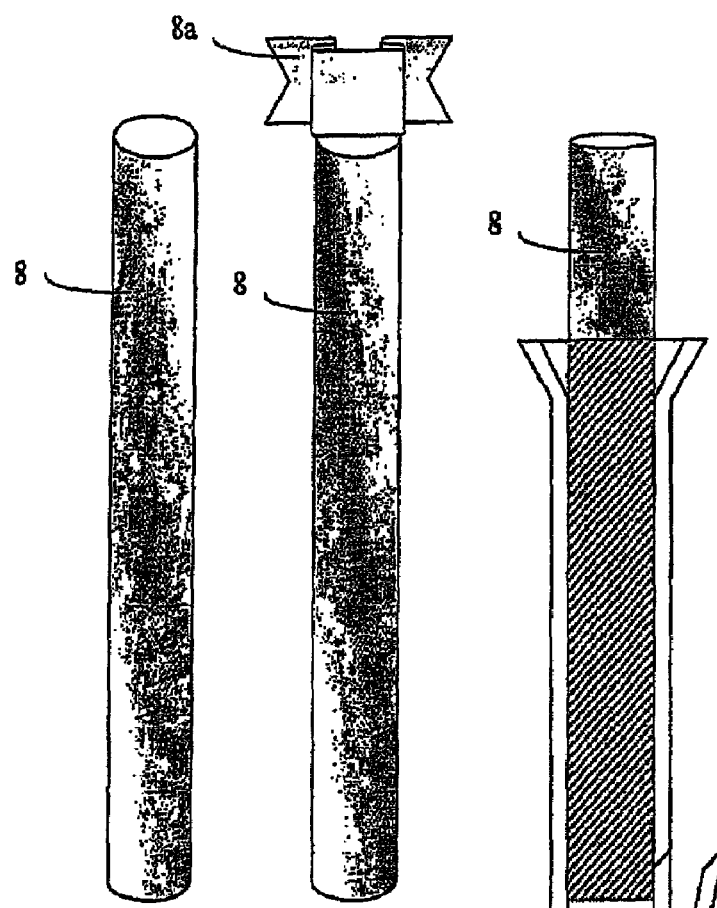
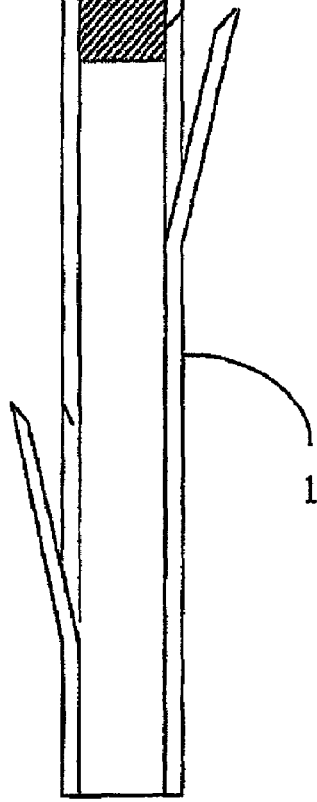
Fig. 3A     Fig. 3B
Fig. 3C

POLYMERIC STENT USEFUL FOR THE TREATMENT OF THE SALIVARY GLAND DUCTS AND METHOD FOR USING THE SAME

RELATED APPLICATIONS

The present application is a Continuation of U.S. application Ser. No. 10/507,304 filed Sep. 10, 2004, now U.S. Pat. No. 7,195,646. U.S. application Ser. No. 10/507,304 claims priority from International Application No. PCT/IL02/00861, filed Oct. 28, 2002, and Israeli Application Serial Number 148616, filed Mar. 11, 2002, the disclosure of which is hereby incorporated by reference herein in its entirety.

FIELD OF THE INVENTION

The present invention relates to a medical device especially useful for surgical endoscopy and treatment of the salivary gland ducts. More specifically, the present invention relates to a stent-like a polymeric device comprising an elastic elongated tube; a funnel attached to said tube, comprising at least one gorge; and at least one flap, having means to anchor said stent to the salivary gland duct to be treated. The present invention also relates to a method for implanting said stent in the salivary gland duct.

BACKGROUND OF THE INVENTION

Abnormalities and pathologies of the salivary glands are traditionally divided into four categories: (i) inflammations; (ii) infections, and (iii) obstruction to the flow of saliva and (iv) tumors. This obstruction is most commonly from the submandibular parotid and glands, usually due to stone formation and due to the presence of strictures and kinks in the salivary gland ducts.

A polyethylene tube, made of a commercially available intravenous catheter (inner diameter of 1.7 to 2.0 mm, length 45 mm) was implanted by Nahelieli et al. (see Nahlieli et al., *J. Oral Maxillofac. Surg.*, 59:484-490, 2001) inside kinked and strictured salivary gland ducts, for two weeks. The anterior edge of this rigid tube was sutured to the mucosa ands the periosteum near the lingual side of the anterior teeth. This preliminary stent-like conduit is characterized by many drawbacks hereto described. It does not enable the continuous drainage of saliva from the oral cavity towards the salivary gland. The immobilization of this polyethylene pipe into the injured salivary gland duct, by means of suturing it to the tissue, is tedious and inefficient. This device is not adapted to be anchored to said salivary duct, so the stent has an unstable location and thus might occasionally damage the salivary duct. Still, this rigid tube can escape from the salivary duct towards the oral cavity or the salivary gland itself and hence might produce a serious injury of these delicate organs. Lastly, and most importantly, the rigidity of the tube and its inefficient design causes severe pain to the patient.

SUMMARY OF THE INVENTION

The present invention provides a polymeric stent, especially useful in surgical endoscopy and for the treatment of salivary gland ducts comprising; an elongated tube, wherein the proximal end of said tube has a funnel-like shape; and wherein said funnel further comprises at least one gorge, which enables the suturing of said stent to said duct.

It is also provided, according to another preferred embodiment of the present invention, a polymeric stent as defined above, having means to be at least temporally anchored inside the lumen of a salivary duct. According to a preferred embodiment of the present invention, said means to encore said stent inside the lumen of the salivary gland duct is at least one wing-like flap and/or said stent comprising two wing-like flaps.

Figure 2A:
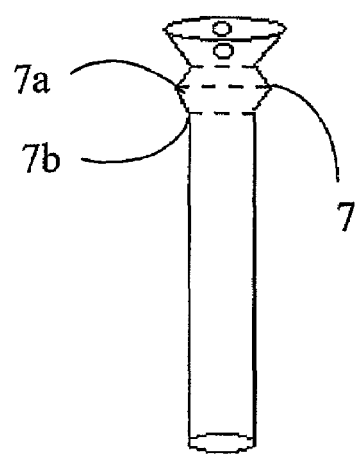

It also provides, according to another preferred embodiment of the present invention, a polymeric stent as defined above, adapted to be at least temporally anchored inside the lumen of a salivary duct, wherein the tube additionally comprises at least one extended portion on its width. One particular embodiment is wherein the extended portion is an accordion-like member, as described in FIG. 2A, and/or a polymeric stent as defined above, additionally comprising a plurality of flaps, arranged in a circular array of folded flaps, as described in FIG. 2C.

It also provides, according to another preferred embodiment of the present invention, a polymeric stent as defined above, in the length of approximately 20 to 65 mm and most particularly in the range of 32 to 48 mm.

It also provides, according to another preferred embodiment of the present invention, a polymeric stent as defined above, wherein the internal diameter of the elongated tube is in the range of approximately 1.0 to 4.5 mm and most particularly in the range of approximately 1.5 to 3.0 mm.

It also provides, according to another preferred embodiment of the present invention, a polymeric stent as defined above, wherein the length of the funnel-like member is in the range of approximately 1.0 to 4.5 mm and most particularly in the range of approximately 1.0 to 4.5 mm.

It also provides, according to another preferred embodiment of the present invention, a polymeric stent as defined above, wherein the tube is selected from a porousive or a non-porousive article, made by the method selected from knitting or weaving a polymeric sleeve; extruding, cast-forming or press-molding a polymeric raw-material.

According to another preferred embodiment of the present invention, a polymeric stent as defined above is provided, suitable for either local or systemic delivery of compounds selected from drugs and other substances.

Still according to another preferred embodiment of the present invention, a polymeric stent as defined above is provided, wherein the drug to be delivered is selected from one or more biocides, steroidal anti-inflammatory agents, antiviral compound, analgesics, local anesthetics, anticoagulants, antihypertensive substances, vitamins and contrast media. More specifically, said biocide to be delivered is selected from cetylpyridinium chloride, benzalkonium chloride, chlorhexidine, cetyltrimethylammonium bromide, polyoxyethylene, nonylphenols, alkylaryl sulfonates, miconazole nitrate, metronidazole, trimethoprim, chloramphenicol, sulfamethoxazole; cetramide or any effective antibiotic. Additionally, amore specifically, the steroidal anti-inflammatory agents to be delivered are selected from corticosteroids and any hydrocortisone containing compositions. Moreover, said local anesthetic is preferably selected from lidocaine, adrenaline, ephedrine, epinephrine, aminophylline, and theophylline.

It also provides, according to another preferred embodiment of the present invention, a polymeric stent as defined above, having means to be temporally anchored to said stent inside the lumen of the salivary gland duct to be treated, comprising a funnel with two gorges. Preferably, said stent is the one described in FIG. 2.

According to another preferred embodiment of the present invention, a method for implanting the polymeric stent into the lumen of a salivary gland duct as defined above is proivided, comprising; (a) inserting said stent into a salivary gland duct to be treated, such that the whole tube is located in said duct and such that the proximal side of said stent is located inside the oral cavity; and (b) suturing said stent to the mucosa and/or the periosteum near the lingual side of the anterior teeth by means of sutures, wherein said sutures are sutured to at least one gorge located in the funnel.

A suitable guidance member may alternatively provide said method. Thus, a method for implanting the polymeric stent into the lumen of a salivary gland duct as defined above is provided in the present invention, wherein the implanting the polymeric stent into the lumen of a salivary gland duct as above, is aided with a relatively rigid guidance member. Said method comprising mainly the hereto define steps of: (a) inserting an effective portion of said guidance member into the tube of the stent at its proximal end; (b) inserting said stent into a salivary gland duct to be treated, such that all of the tube is located in said duct and such that the proximal side of said stent is located inside the oral cavity; (c) removing said guidance member from the stent; and (d) suturing said stent to the mucosa and/or the periosteum near the lingual side of the anterior teeth by means of sutures, wherein said sutures are sutured to at least one gorge located in the funnel.

It also provides, according to another preferred embodiment of the present invention, a method for implanting the polymeric stent into the lumen of a salivary gland duct as defined above, especially useful for the treatment of strictures, kinks, and any pathology of the salivary gland duct, wherein said method is especially useful for practice along and after a surgical endoscopy.

Lastly, it also provides, according to another preferred embodiment of the present invention, a method for implanting the polymeric stent into the lumen of a salivary gland duct as defined above, wherein said treatment by the polymeric stent defined in claim 1 and in preceding claims is for a period of approximately two weeks.

BRIEF DESCRIPTION OF THE INVENTION

FIGS. 1A and 1B respectively present a side-view of a polymeric stent comprising an elongated tube, attached funnel, two gorges and two flaps (FIG. 1A), and a top view of said stent.

FIG. 2 presents a side view of various stents according to the present invention.

FIG. 3 presents a side view of a polymeric stent with a guidance member, and two possible guidance members.

FIG. 4 presents a method for implanting the polymeric stent into the lumen of a salivary gland duct with an aided of a guidance member. The method is schematically comprising the steps of inserting an effective portion of the guidance member into the tube of the stent at its proximal end (A), so the guidance member is strongly anchored inside the bore of the stent (B); inserting said stent into a salivary gland duct to be treated, such that all of the tube is located in said duct and such that the proximal side of said stent is located inside the oral cavity (C); and then removing said guidance member from the stent (D).

DETAILED DESCRIPTION OF THE INVENTION

The current invention contemplates the usage of any prosthesis, which can be inserted into the saliva duct in order to create a continuous passageway through said duct. When "stent" is referred to herein, it may include the classical definition of stents as they are used in known intravascular applications. "Stent" used herein also includes any prosthesis which may be inserted and held where desired in the lumen of said saliva duct.

The following description is provided, along all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide for stenting and supporting the continuous flow of saliva throughout the saliva ducts.

There are several polymeric compounds that are known to be bioabsorbable and to have the ability to be drug impregnated. These compounds include, yet not limited to poly-1-lactic acid, polyglycolic acid, polyanhydride, and polyphosphate ester, polyurethanes, polyethylene. Most specifically, theromplastic polyurethanes, such as the commercially available Estane products (such as Estane 58092), are suitable as raw-martials for the hereto-defined stent. It is further acknowledged that various coloring materials and surface coatings are suitable for use. Those raw materials may be used in their many forms, i.e., crystals, fibers, blocks, plates, etc. and in a wide range of molecular weights. Co-polymers and blends are applicable according to the present invention to form either porous or non-porous polymeric stents. The polymeric stents, according to the present invention, may be made as an extruded open-bore polymeric pipe, a woven or knitted sleeve etc. According to a preferred embodiment of the present invention, extrusion, cast-forming or press-molding techniques are suitable for the production of the polymeric stent.

Additionally, according to a preferred embodiment of the present invention, said polymeric composition of the stent may be bio-stable or bio-absorbable. If bio-stable, a drug, as wildly defined in the present invention, would diffuse out of the polymer. Various compositions are suitable to be delivered either locally or systematically by the aforementioned polymeric stent. These release compositions are selected for drugs, and any other desired materials, including, yet not limited to one or more biocides, steroidal anti-inflammatory agents, antiviral compound, analgesics, local anesthetics, anticoagulants, antihypertensive substances, vitamins and contrast media.

According to another preferred embodiment of the present invention, steroidal anti-inflammatory agents may be used, comprising, but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

According to another preferred embodiment of the present invention, at least two antiviral compounds may be used, comprising, but not limited to acyclovir and interferon.

According to another preferred embodiment of the present invention, steroidal analgesics may be used, comprising, but not limited to aspirin, salicylic acid, diflunisal, morphine and its salts and the like.

According to another preferred embodiment of the present invention, antiseptic substances may be used, comprising, but not limited to cetylpyridinium chloride, benzalkonium chloride, chlorhexidine and the like.

According to another preferred embodiment of the present invention, antimycotic substances may be used, comprising, but not limited to cetyltrimethylammonium bromide and the like.

According to another preferred embodiment of the present invention antifungals, may be used, comprising, but not limited to polyoxyethylene nonylphenols, alkylaryl sulfonates, miconazole nitrate, metronidazole, trimethoprim and the like.

According to another preferred embodiment of the present invention, antiprotozoals may be used, comprising, but not limited to chloramphenicol, sulfamethoxazole and the like.

According to another preferred embodiment of the present invention, local anesthetics may be used, comprising, but not limited to salts of procaine, benzocaine, lidocain, procain, bupivacaine, tetracain, xylocaine, mepivacaine and their salts and the like; antiasthma drugs such as adrenaline, ephedrine, epinephrine, aminophylline, theophylline and the like.

According to another preferred embodiment of the present invention anticoagulants, may be used, comprising, but not limited to heparin and its salts, such as calcium and sodium heparin, bishydroxycoumarin and the like.

According to another preferred embodiment of the present invention antihypertensive, may be used, comprising, but not limited to methyldopa, hydralazine, clonidine, chlorothiazide, timolol, propanolol, metroprolol, prazosin hydrochloride, furosemide and the like.

According to another preferred embodiment of the present invention, vitamins may be used, comprising, but not limited to such as $B_6$, $B_{12}$ and C and the like.

According to another preferred embodiment of the present invention contrast media, may be used, comprising, but not limited to $BaSO_4$, iohexol and other iodine-containing substances and the like (x-ray), iron(II,III)oxide particles, titanium dioxide pigments, and other ferromagnetic materials (magnetic resonance imaging). It is acknowledged in this respect, that various coloring materials, such as 14-4007 PV fast violet pigments, are possible ingredients of the material forming or coating the stents.

Reference is made now to FIG. 1, presenting one preferred embodiment of the polymeric stent according to the present. Said stent comprises an elongated open-bore polymeric tube (1), comprising a proximal rim (i) located adjacent to the oral cavity when implanted in the salivary gland duct, and a distal rim (ii), located adjacent to the salivary gland when implanted in the salivary gland duct. The aforementioned stent additionally comprises a funnel (2), located in the proximal rim of said tube. The inner diameter of said tube at the proximal rim is equal to the inner diameter of the funnel at its distal rim (4), wherein the inner diameter of the funnel at the proximal rim is wider than at the distal rim (3). Said funnel is preferably comprises of at least one gorge, which is a hole in the wall of said funnel, that enables the surgeon implanting said stent to suture it easily and efficiently. The stent might comprise a few gorges, wherein two gorges are sufficient to anchor the stent in its desired location inside the salivary gland duct.

Additionally or alternatively, the stent according to the present invention, comprises at least one flap, ensuring that the stent is fixed to its desired position without any undesirable movement along the salivary gland duct. FIG. 1B present a top view of the stent, takes from the proximal rim (3) of the stent to its distal end (4), comprising two gorges (5a, 5b). It is acknowledged that the hereto-described stent may comprise between one to four gorges. Nonetheless, more gorges are possible, and may be useful in some cases.

Reference is made now to FIG. 2, presenting preferred embodiments of the hereto-defined polymeric stent. FIG. 2A is a side view of a stent according to the present invention, comprising an accordion-shaped extension (7). The external diameter of said extension (7a) is wider than the external diameter of said elongated tube (7b), thus enabling the fixation of the stent inside the lumen of the salivary gland duct. It is acknowledged that more than one of said extension is possible and a few said extensions may be useful in some specific lumens.

Figure 2B:
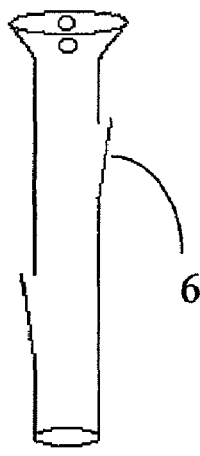

FIG. 2B presents a side-view of the stent according to the present invention, wherein at least one flap (6) is provided for enabling the stent to be affixed inside the salivary gland duct. Said flap is preferably a leaf-like polymer made article, comprising considerable elasticity which ensures efficient and consistent attachment to the interior lumen of the salivary gland duct to be treated. It is acknowledged that more than one flap is possible, and a set of a few flaps may be useful in some specific lumens. The flaps may be arranged side-by-side (e.g., in parallel), or one along the other as described in the aforementioned FIG. 2B.

Figure 2C:
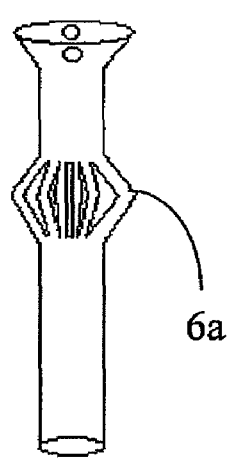

Referring now FIG. 2C, the stent according to the present invention comprises at least one circular array of folded flaps (6a). It is appreciated that the external diameter of the folded flaps is wider than the external diameter of the elongated tube, whereby the fixation of the stent inside the lumen of the salivary gland duct. It is further acknowledged that more than one circular array of folded flaps (6a) is possible, and a set of a few of said arrays may be useful in some specific lumens.

Figure 2D:
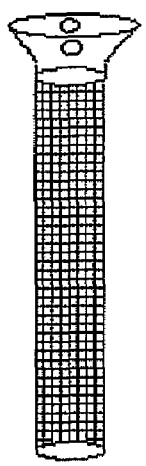
Figure 4A:
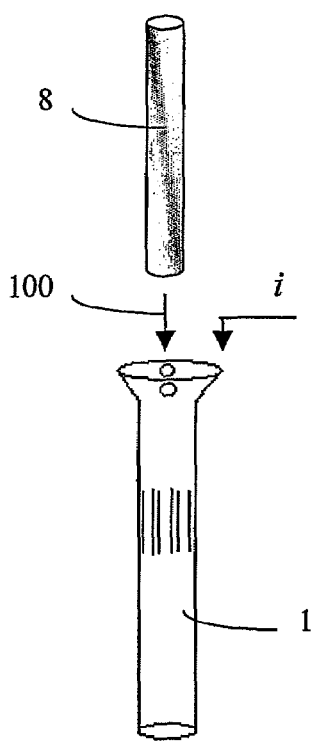
Figure 4B:
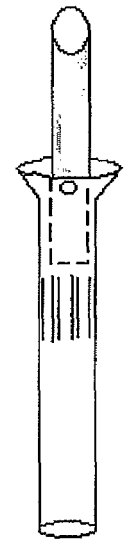
Figure 4C:
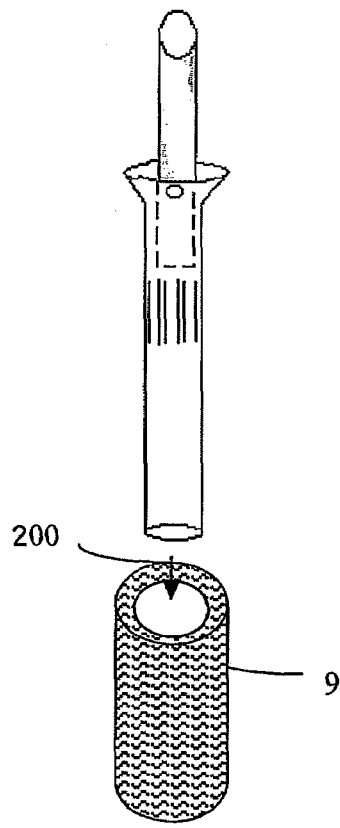
Figure 4D:
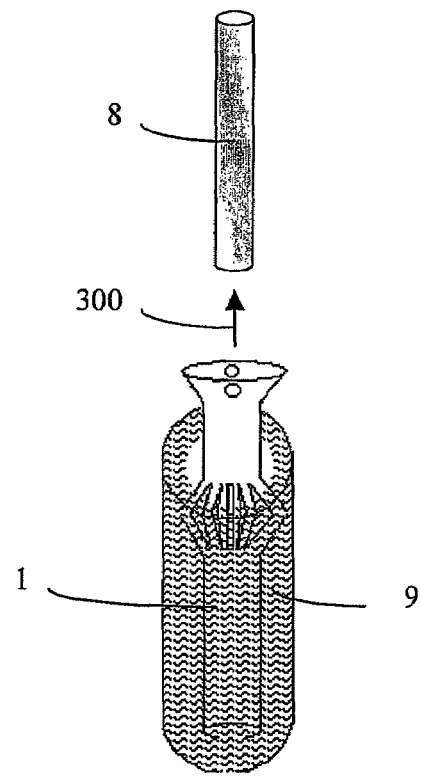

FIG. 2D presents a side-view of a simple polymeric stent according to the present invention, wherein the stent in affixed to the interior lumen of the salivary gland duct, only by means of suturing the stent to tissues located in the oral cavity. Moreover, as schematically described in FIG. 2D, the surface of the stent, and more particularly, the walls of the polymeric tube portion of said stent might comprise porous. Thus, according to one preferable embodiment of the present invention, the aforementioned stent is made as an elongated sleeve, made of either porousive open-bore pipe, which was reshaped by pressure-molding, by knitting or weaving extruded polymeric fibers or by any other suitable technique.

Reference is still made to FIG. 3, schematically presenting two guidance members (8). The first member is a relatively rigid tube (A) and the second member is adapted to be conveniently inserted inside the tube (1) of the stent. Draw C shows the polymeric stent (1) wherein the guidance member (8, as shown in draw A) is partially inserted into the proximal rim of the stent.

Reference is lastly made to FIG. 4, schematically presenting a method for implanting the polymeric stent according to the present invention into the lumen of a salivary gland duct (9) with an aided of a guidance member (8). Said guidance member is preferably made of relatively rigid materials, such as polymers (e.g., polymethyl metaactrylate or other acrylates, high-density polyethylene, high-density polypropylene, high-density polystyrene etc.), rubber made articles, or any suitable metal wares. In one preferred embodiment, said guidance member is an elongated tube with an external diameter, which is approximately equal to the internal diameter of the stent's tube (1). This guidance member (8) is preferably sterilezable member, adapted to be held conveniently by the surgeon (See for example FIG. 3B).

The method for the deployment of said stent is schematically presented in FIG. 3 and comprising the steps of inserting (100) an effective portion of the guidance member (8) into the tube (1) of the stent at its proximal end (i) (FIG. 3A), so the guidance member is strongly anchored inside the bore of the stent (FIG. 3B); inserting (200) said stent into a salivary gland duct to be treated, such that all of the tube is located in said duct (9) and such that the proximal side of said stent is located inside the oral cavity (FIG. 3C); and then removing (300) said guidance member (8) from the stent (FIG. 3D) whereas the stent is still anchored inside the lumen (8).

The invention claimed is:

1. A polymeric stent adapted for implantation in a salivary gland duct of an oral cavity, said stent being an elongate member and comprising
    an enlarged funnel-like proximal portion at a proximal end of the stent; and
    a bore extending through said stent from said proximal end to a distal end of the stent;
    said enlarged proximal portion comprising:
    a proximal rim adapted for being located adjacent the oral cavity; and
    at least one aperture adapted for suturing said stent to said oral cavity when said stent is implanted in a said salivary gland duct;
    said elongate member comprising at least one wing-like flap and a plurality of axially folded flaps arranged in a circular array.

2. The stent according to claim 1, wherein said at least one wing-like flap comprises a free end spaced from a surface of the elongate member.

3. The stent according to claim 1, wherein said enlarged proximal portion comprises a substantially continuous proximal rim.

4. The stent according to claim 3, wherein said enlarged proximal portion comprises an axial length of between about 1.0 mm and about 4.5 mm.

5. The stent as defined in claim 1, comprising a plurality of said flaps arranged on said elongate member.

6. The stent as defined in claim 5, wherein said flaps are axially folded and arranged in a circular array.

7. The stent according to claim 1, having an axial length of between about 20 mm and about 65 mm.

8. The stent according to claim 1, having an axial length of between about 32 mm and about 48 mm.

9. The stent as defined in claim 1, wherein said bore comprises an internal diameter of between about 1.0 mm and about 4.5 mm.

10. The stent according to claim 1, wherein said bore comprises an internal diameter of between about 1.5 mm and about 3.0 mm.

11. The stent according to claim 1, wherein the stent is made from a suitable polymeric material.

12. The stent according to claim 11, wherein the stent is made from any one of: poly-1-lactic acid, polyglycolic acid, polyanhydride, polyphosphate ester, polyurethanes, polyethylene.

13. The stent according to claim 11, wherein the stent is made from one of a porous or a non-porous polymeric rawmaterial.

14. The stent according to claim 1, wherein the stent is made from one of a bio-stable and a bioabsorbable material adapted for at least one of local and systemic delivery of compounds selected from at least one of drugs and other substances.

15. The stent according to claim 14, wherein the stent comprises said compound, said compound comprising a drug to be delivered is selected from one or more biocides, steroidal anti-inflammatory agents, antiviral compounds, analgesics, local anesthetics, anticoagulants, antihypertensive substances, vitamins and contrast media.

16. The stent according to claim 14, wherein the stent comprises said compound, said compound comprising a biocide selected from cetylpyridinium chloride, benzalkonium chloride, chlorhexidine, cetyltrimethylammonium bromide, polyoxyethylene, nonylphenols, alkylaryl sulfonates, miconazole nitrate, metronidazole, trimethoprim, chloramphenicol, sulfamethoxazole; cetramide or any effective antibiotic.

17. The stent according to claim 14, wherein the stent comprises said compound, said compound comprising a steroidal anti-inflammatory agents to be delivered are selected from corticosteroids and any hydrocortisone containing compositions.

18. The stent according to claim 14, wherein the stent comprises said compound, said compound comprising a local anesthetic selected from lidocaine, adrenaline ephedrine, epinephrine, aminophylline, and theophylline.

19. A stent system, comprising a stent according to claim 1 and a guidance member comprising a substantially rigid member adapted for being accommodated within said bore of the stent.

* * * * *